United States Patent [19]

Janchipraponvej

[11] Patent Number: 4,954,335

[45] Date of Patent: Sep. 4, 1990

[54] CLEAR CONDITIONING COMPOSITION AND METHOD TO IMPART IMPROVED PROPERTIES TO THE HAIR

[75] Inventor: Ben Janchipraponvej, Niles, Ill.

[73] Assignee: Helene Curtis, Inc., Chicago, Ill.

[21] Appl. No.: 359,483

[22] Filed: May 31, 1989

[51] Int. Cl.$^5$ .............................................. A61K 7/075
[52] U.S. Cl. ..................................... 424/070; 514/788; 514/772; 514/789
[58] Field of Search .................. 424/70; 514/788, 789, 514/772

[56] References Cited

U.S. PATENT DOCUMENTS

| | | |
|---|---|---|
| 4,726,945 | 2/1988 | Patel et al. ............................. 424/70 |
| 4,777,037 | 10/1988 | Wagman et al. .................. 424/71 X |
| 4,818,523 | 4/1989 | Clarke et al. ......................... 424/70 |

*Primary Examiner*—Merrell C. Cashion, Jr.
*Assistant Examiner*—Susan S. Rucker
*Attorney, Agent, or Firm*—Marshall, O'Toole, Gerstein, Murray & Bicknell

[57] ABSTRACT

A method of imparting improved conditioning properties to hair comprising treating the hair with a clear conditioning composition comprising a quaternary ammonium compound, such as dicetyldimonium chloride; an amidoamine compound having the general formula:

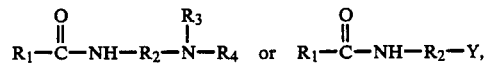

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety, like morpholine or pyridine; a volatile conditioning agent, such as a volatile hydrocarbon compound or a volatile silicone compound, like cyclomethicone; a solubilizing nonionic surfactant, like lauryl pyrrolidone; and a polyhydric compound, such as a glycol, a triol or a polyol, like hexylene glycol. The clear conditioning composition unexpectedly provides improved hair-conditioning properties, such as wet and dry feel, wet and dry combing, less coating, increased body and overall hair condition to treated hair.

35 Claims, No Drawings

CLEAR CONDITIONING COMPOSITION AND METHOD TO IMPART IMPROVED PROPERTIES TO THE HAIR

FIELD OF THE INVENTION

The present invention relates to a clear hair-treating composition and to a method of treating hair that unexpectedly imparts improved conditioning properties to hair. More particularly, the present invention is directed to a clear hair-treating composition comprising from about 0.5% to about 5% by weight of a quaternary ammonium compound, such as dicetyldimonium chloride; from about 0.1% to about 5% by weight of an amidoamine compound having the general structural formula (I) or (II):

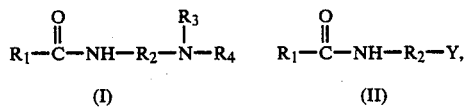

$$R_1-\overset{O}{\underset{\|}{C}}-NH-R_2-\overset{R_3}{\underset{|}{N}}-R_4 \quad\quad R_1-\overset{O}{\underset{\|}{C}}-NH-R_2-Y,$$

(I)  (II)

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety, like morpholine or pyridine; from about 0.5% to about 5% by weight of a volatile conditioning agent, such as a volatile hydrocarbon compound or a volatile silicone compound, like cyclomethicone; from about 1% to about 10% by weight of a solubilizing nonionic surfactant, like lauryl pyrrolidone; and from about 10% to about 30% by weight of a polyhydric compound, such as a glycol, triol, or polyol, like hexylene glycol; and wherein the weight ratio of solubilizing nonionic surfactant to volatile conditioning agent in the composition ranges from about 1 to 1 to about 10 to 1. The clear composition of the present invention can be applied to the hair from an aqueous solution or spray, a conditioner formulation, a hair color and/or other similar hair treatment products, over a pH range of from about 4 to about 7, to improve both the wet stage and the dry stage properties of the hair.

BACKGROUND OF THE INVENTION

Most individuals buy and use a hair shampoo for its cleansing properties. In addition to having clean hair, the consumer also desires sufficiently-conditioned hair that holds a preset configuration. However, hair shampoos generally are formulated with highly effective synthetic surfactants, like anionic surfactants, that primarily clean as opposed to conditioning the hair. Therefore, shampoos usually neither aid in the detangling of wet hair nor impart any residual conditioning benefits to dry hair, such as manageability or styleability of hair sets.

Consequently, the hair normally is left in a cosmetically-unsatisfactory state after washing with an anionic surfactant-based hair shampoo. Anionic surfactants not only remove the dirt and soil from the hair, but also remove essentially all of the sebum naturally present on the surface of the hair fibers. Therefore, it was found that the desirable properties of anionic surfactants that effectively clean the hair also serve to leave the hair in a cosmetically-unsatisfactory condition. In general, hair shampoo compositions containing anionic surfactants, or nonionic surfactants or amphoteric surfactants, leave the hair with an undesirable harsh, dull and dry touch, or feel, usually called "creak", after the hair is shampooed and then rinsed with water.

Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. Furthermore, the combing or brushing property of the hair remains poor, and the hair has undesirable electrostatic properties in a low humidity atmosphere that causes the hair to "fly away", thereby further reducing the brushing properties of the hair. The unsatisfactory combing or brushing property of hair immediately after shampooing, or during trimming treatments after shampooing, also causes hair damage, such as split ends or hair breakage. In addition, the natural luster and resiliency of the hair is reduced. Consequently, the overall unsatisfactory condition of the shampooed hair usually necessitates a subsequent post-shampoo treatment of the hair with a special conditioning composition to improve these undesirable physical characteristics. These conditioning compositions normally are applied separately from the hair shampoo, and usually are rinses or cream-like emulsions or lotions containing a cationic compound.

Therefore, consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition, followed by a second rinse. As previously discussed, freshly shampooed hair is inclined to knot and tangle, and therefore is difficult to comb and difficult to manage. The wet combing problem has been solved by treating shampooed hair with a conditioner composition that coats the hair shaft and causes the individual hair shafts in a tress to resist tangling and matting because of the conditioner residue retained on the shaft.

However, the need for improved compositions that condition the hair, i.e., renders the hair more manageable, has long been recognized in the art. As previously discussed, it is well-known that anionic surfactants are suitable for hair shampooing, and that cationic compounds, like cationic surfactants and cationic polymers, are useful as hair conditioners. Therefore, cationic compounds that are substantive to hair usually are used to complete the hair cleansing and hair conditioning cycle.

The ability of cationic compounds to adsorb or react with the keratinous material of the hair makes them the most desirable compounds for imparting the desired improvement in wet hair detangling and dry hair manageability. However, hair conditioning compositions including cationic compounds that adsorb particularly strongly to the hair also can reduce the elasticity, body and set of the dried hair. Therefore, although conditioning compositions for application to freshly shampooed hair are well known, new and improved conditioning formulations based on cationic compounds are continually sought. For example, the majority of present-day, commercial hair-conditioner compositions are emulsion-type products that leave too great of a conditioning-compound residue on the hair. Consequently, the present invention is directed to a new, non-emulsified, clear hair-conditioning composition comprising a combination of suitable hair-conditioning ingredients that is esthetically acceptable to consumers, improves the wet combing and dry combing properties of hair, and also leaves the dry hair with satisfactory cosmetic properties and physical properties, including, in particular, dry combing and feel, less hair coating, manageability, body, condition of the ends and set.

Hair conditioning compositions, such as emulsion-type creme rinses, are well known in the art for improving the combing properties of wet hair and dry hair. These conditioning compositions typically are aqueous emulsions including a cationic compound, like a quaternary ammonium compound, as the principal conditioning agent. The prior art describes the quaternary ammonium compound either as a polymeric material having a plurality of quaternary nitrogen atoms per molecule or as a molecule having at least one long carbon atom chain and an average of one quaternary nitrogen atom per molecule. The prior art also describes hair conditioning compositions as including silicon-containing compounds, substituted amines and amides, nonionic surfactants, long carbon chain alcohols, and other ingredients to facilitate composition formulation and enhance consumer appeal.

For example, U.S. Pat. No. 3,993,744 to Cella et al discloses that cationic compounds, such as quaternary ammonium compounds, and silicones can be combined with perfluorinated compounds to provide hair treatment compositions. The silicones specifically disclosed by Cella et al are surfactant-like polyoxyethylene polymethylsiloxanes that are presumed to be water-soluble or dispersible. According to Cella et al, both the quaternary ammonium compounds and the silicones are utilized in relatively small amounts, e.g., about 0.05 weight percent of the composition. Other prior art patents disclosing the use of silicones having viscosities greater than about 100 centistokes at 25° C. to provide lubricity or sheen to various cosmetic preparations, include U.S. Pat. Nos. 2,942,008; 3,594,409; 3,824,303; and 4,014,995.

Matravers, in U.S. Pat. No. 4,725,433, discloses a clear conditioning composition comprising an aqueous blend of a polymeric quaternary ammonium salt, ethoxylated lauryl alcohol, ethoxylated cholesterol and hydroxyethylcellulose. However, each of the ingredients included in the Matravers composition is water-soluble or water-dispersible. The volatile conditioning agent utilized in the present invention, such as a volatile silicone or a volatile hydrocarbon, is water insoluble, and, therefore, is the most difficult component of the composition to solubilize. The composition disclosed by Matravers does not include a water-insoluble, volatile conditioning agent, and there is no suggestion or teaching of the desirability of including a water-insoluble conditioning agent in the composition disclosed in U.S. Pat. No. 4,725,433.

British Patent No. 1,598,567 further discloses the use of a linear or a cyclic, volatile polydimethylsiloxanes, i.e., having a boiling point in the range of 99° C. to 265° C., in hair conditioning compositions. The composition of British Patent No. 1,598,567 is described as avoiding the formation of an oleophilic hair surface that usually occurs when using a quaternary ammonium hair conditioning agent. South African patent application No. 666,421 also teaches the use of compositions containing straight chain and volatile cyclic silicone fluids to provide gloss and conditioning effects to hair dressings.

Nachtigal et al, in U.S. Pat. No. 4,275,055, discloses a pearlescent hair conditioner composition including a quaternized tertiary amidoamine, a quaternary ammonium compound and, optionally, a tertiary amidoamine, i.e., stearamidoethyldiethylamine. The composition of Nachtigal et al is directed to achieving a stable pearlescent effect and neither includes a volatile conditioning agent nor is the composition a clear conditioning composition that demonstrates the improved rinsability of the clear hair-treating composition of the present invention.

Bolich et al, in U.S. Pat. No. 4,374,825, discloses an aqueous hair conditioning composition comprising a volatile hydrocarbon or volatile silicone, a cationic hair conditioning agent and a nonionic thickening agent. Similarly, Bolich et al in U.S. Pat. No. 4,472,375, discloses a hair conditioning composition comprising a volatile hydrocarbon or a volatile silicone, a nonionic thickening agent, a quaternary ammonium salt and a salt of a fatty amine. Neither Bolich et al patent teaches or suggests using a combination of a solubilizing nonionic surfactant with a polyhydric compound to completely solubilize the volatile conditioning agent to provide the unexpectedly efficacious, clear hair-conditioning composition of the present invention. Bolich, in U.S. Pat. No. 4,387,090, also discloses a hair-conditioner composition comprising a volatile hydrocarbon or a volatile silicone conditioning agent and a hydrophobic thickening agent. Other prior art references relating to the use of a volatile conditioning agent in hair-conditioning compositions include U.S. Pat. Nos. 3,577,528; 3,932,610; and 3,818,105.

Coopersmith in U.S. Pat. No. 3,818,015 discloses that $C_{12}$ to $C_{14}$ isoparaffinic hydrocarbons, when combined with naphthenic materials, are useful in a wide range of cosmetic formulations. Such paraffinic hydrocarbons lubricate the skin to achieve a quick spreading, non-greasy application of the product, with evaporation of the hydrocarbon after application to avoid a greasy buildup.

Japanese TKS No. 57-50909 discloses a hair conditioner composition comprising a volatile silicone and a combination of two water-insoluble quaternary ammonium salts, wherein each quaternary ammonium salt includes two long chain alkyl groups. Japanese TKS No. 57-50909 does not teach or suggest using an amidoamine compound in a composition to impart unexpected hair conditioning properties to hair or the desirability of solubilizing a water-insoluble volatile conditioning agent to provide a clear hair-conditioning composition.

Wagman et al in U.S. Pat. No. 4,777,037 discloses a hair conditioner composition comprising a polydimethyl cyclosiloxane, a quaternary-nitrogen containing conditioning agent having two long alkyl chains of twelve to eighteen carbons and two short alkyl chains of one or two carbon atoms, a long chain fatty alcohol and a tertiary amidoamine of the general structural formula (III):

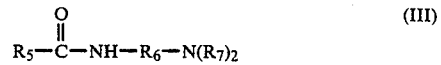

wherein $R_5$ is a fatty chain having from about 11 to about 17 carbon atoms, $R_6$ is an alkylene group having 2 or 3 carbon atoms and $R_7$ is either methyl or ethyl. The compositions of Wagman et al are emulsions as opposed to the clear hair-conditioning compositions of the present invention that demonstrate improved rinsability from the hair and that impart exceptional conditioning properties to the hair while coating the hair with less of the quaternary ammonium compound and the volatile conditioning agent.

As will be demonstrated more fully hereinafter, and in contrast to prior art, emulsion-type hair-conditioning compositions, a clear hair-conditioner composition of the present invention, comprising a quaternary ammonium compound, a volatile conditioning agent, an amidoamine compound of general structural formula (I) or (II), a solubilizing nonionic surfactant and a polyhydric compound, unexpectedly exhibits improved rinsability from the hair and imparts improved conditioning properties upon application to human hair. Therefore, in accordance with the present invention, hair conditioning properties are surprisingly and unexpectedly improved by a method of contacting the hair with a clear composition comprising a quaternary ammonium compound, a volatile conditioning agent, an amidoamine compound of general structural formula (I) or (II), a solubilizing nonionic surfactant and a polyhydric compound. The compositions of the present invention can be applied to the hair from an aqueous vehicle at ambient temperature and are allowed to contact the hair for relatively short times to provide the benefits and advantages of a hair conditioner. Consequently, the method and composition of the present invention condition the hair to provide more manageable and esthetically-pleasing hair.

SUMMARY OF THE INVENTION

In brief, the present invention relates to a composition and method of treating hair. More particularly, the present invention relates to a method of treating the hair, whereby the hair is conditioned by contacting the hair with a clear, homogeneous composition comprising (a) a quaternary ammonium compound; (b) a volatile conditioning agent, such as a volatile silicone, like a low molecular weight polydimethylsiloxane compound; (c) an amidoamine compound, wherein the amidoamine compound has the general structural formula (I) or (II):

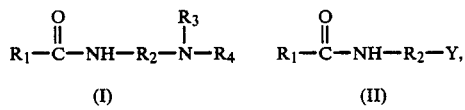

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety; (d) a solubilizing nonionic surfactant; and (e) a polyhydric compound, such as a diol, triol or polyol. The easy-to-apply clear composition imparts excellent wet stage and excellent dry stage conditioning properties to the hair and exhibits improved rinsability from the hair. Surprisingly and unexpectedly, hair treated with the clear composition of the present invention also demonstrates improved physical properties and cosmetic properties, such as wet and dry feel, less coating, wet and dry combing, thickness, overall hair condition, manageability and body. In addition, the clear hair-conditioning composition of the present invention imparts improved conditioning properties to treated hair while coating the hair with less of the quaternary ammonium compound and volatile conditioning agent.

Therefore, it is an object of the present invention to provide a clear hair-treating composition that conditions the hair and imparts improved physical properties and cosmetic properties to the hair.

It is also an object of the present invention to provide a clear hair-treating composition comprising a quaternary ammonium compound; a volatile conditioning agent; an amidoamine compound having general structural formula (I) or (II); a solubilizing nonionic surfactant; and a polyhydric compound.

Another object of the present invention is to provide a clear hair-treating composition that is capable of conditioning the hair and imparting improved physical and cosmetic properties to the hair over a pH range of about 4 to about 7.

Another object of the present invention is to provide a method of treating hair with a clear hair-treating composition to achieve an improved condition of the hair.

Another object of the present invention is to provide a method of treating hair by contacting the hair with a clear composition having a pH of between about 4 and about 7 and comprising a water-soluble quaternary ammonium compound, a volatile polydimethylsiloxane compound or a volatile hydrocarbon compound, an amidoamine of general structural formula (I) or (II), a solubilizing nonionic surfactant and a polyhydric compound; then drying the hair, to condition the hair and to impart improved physical and cosmetic properties to the hair.

Another object of the present invention is to provide a method of treating hair to yield unexpectedly well-conditioned hair by contacting the hair with a clear composition comprising (a) from about 0.5% to about 5% by weight of a quaternary ammonium compound; (b) from about 0.1% to about 5% by weight of a volatile polydimethylsiloxane compound or a volatile hydrocarbon compound; (c) from about 0.1% to about 5% by weight of an amidoamine compound having the general structural formula (I) or (II); (d) from about 1% to about 10% by weight of a solubilizing nonionic surfactant; and (e) from about 10% to about 30% by weight of a polyhydric compound, wherein the weight ratio of solubilizing nonionic surfactant to volatile conditioning agent ranges from about 1 to 1 to about 10 to 1.

Another object of the present invention is to provide a method of treating hair to yield unexpectedly well conditioned hair by contacting the hair with a composition comprising from about 0.5% to about 5% by weight dicetyldimonium chloride; from about 0.1% to about 5% by weight of cyclomethicone; and from about 0.1% to about 5% by weight of stearamidopropyldimethylamine, an amidoamine compound of general structural formula (I) having the structural formula (IV):

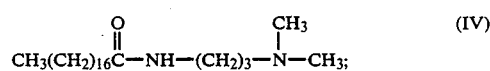

from about 1% to about 10% by weight of an N-alkylated pyrrolidone; and from about 10% to about 30% of hexylene glycol, wherein the weight ratio of N-alkylated pyrrolidone to cyclomethicone is in the range of from about 1 to 1 to about 10 to 1.

Another object of the present invention is to provide a new and improved clear hair conditioning composition capable of conditioning the hair and imparting improved physical, cosmetic and esthetic properties both to normal hair and to tinted, frosted, bleached or other substantially-damaged hair.

Still another object of the present invention is to provide a method of treating the hair to yield unexpectedly well-conditioned hair having esthetically-pleasing physical properties by contacting the hair with a clear, aqueous spray or solution to treat the hair, without heat, in either a rinse-off or leave-on method.

DETAILED DESCRIPTION OF THE PREFERRED EMBODIMENT

The clear hair-conditioning composition of the present invention comprises a (a) quaternary ammonium compound; (b) a volatile conditioning agent, like a low molecular weight polydimethylsiloxane compound or a low molecular weight hydrocarbon compound; (c) an amidoamine compound having the general structural formula (I) or (II):

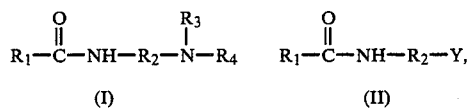

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety, like morpholine or pyridine; (d) a solubilizing nonionic surfactant, like an N-alkylated pyrrolidone; and (e) a polyhydric compound. The easy-to-apply, clear composition provides excellent wet comb and excellent dry comb properties to the hair, and the hair demonstrates improved physical and cosmetic properties, such as gloss, thickness, softness, manageability, body and less coating.

The quaternary ammonium compounds useful in the composition of the present invention preferably are water-soluble quaternary ammonium compounds having one or two long chain alkyl groups containing from about 8 to about 18 carbon atoms. The long chain alkyl groups also can include, in addition to, or in replacement of, carbon and hydrogen atoms, ether linkages or similar water-solubilizing linkages. The remaining two to three substituents of the quaternary nitrogen of the quaternary ammonium compound can be hydrogen; or benzyl; or short chain alkyl or hydroxyalkyl groups, such as methyl, ethyl, hydroxymethyl or hydroxyethyl groups; or combinations thereof, either of the same or of different identity.

However, an oil-soluble, water-dispersible quaternary ammonium compound, either alone or in combination with a water-soluble quaternary ammonium compound also can be used in the composition of the present invention. The oil-soluble quaternary ammonium compounds useful in the composition of the present invention are quaternary ammonium compounds having one or two long chain alkyl groups including from about 14 to about 22 carbon atoms. The remaining two to three substituents present on the quaternary nitrogen of the quaternary ammonium compound can be hydrogen; or benzyl; or short chain alkyl groups, such as methyl, or ethyl; or combinations thereof.

Therefore, the quaternary ammonium compound useful in the present invention is a water-soluble or oil-soluble quaternary ammonium compound, or combinations thereof, depicted by the following general structural formula:

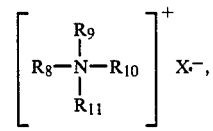

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate. However, it should be noted that the quaternary nitrogen of the quaternary ammonium compound also can be included in a heterocyclic nitrogen-containing moiety, such as morpholine or pyridine.

As previously discussed, quaternary ammonium compounds are well-known hair conditioners. The quaternary ammonium salts are substantive to the hair and provide some of the properties desired in well-conditioned hair. Consequently, several quaternary ammonium compounds have been found useful as hair conditioning agents, and therefore can be used as the quaternary ammonium compound conditioning component in the composition and method of the present invention. Consequently, the following water-soluble quaternary ammonium compounds are exemplary, but not limiting, of water-soluble quaternary ammonium compounds that can be used in the method and composition of the present invention, either alone or in combination:

| | |
|---|---|
| Lauryltrimethylammonium chloride | (Laurtrimonium chloride); |
| Stearyltri(2-hydroxyethyl) ammonium chloride | (Quaternium-16); |
| Lauryldimethylbenzyl-ammonium chloride | (Lauralkonium chloride); |
| Oleyldimethylbenzyl-ammonium chloride | (Olealkonium chloride); |
| Dilauryldimethylammonium chloride | (Dilauryldimonium chloride); |
| Cetyldimethylbenzylammonium chloride | (Cetalkonium chloride); |
| Dicetyldimethylammonium chloride | (Dicetyldimonium chloride); |
| Laurylpyridinium chloride | (Laurylpyridinium chloride); |
| Cetylpyridinium chloride | (Cetylpyridinium chloride); |

| | |
|---|---|
| N-(soya alkyl)-N,N,N-trimethyl ammonium chloride | (Soyatrimonium chloride); |
| Polydiallyldimethylammonium chloride | (Polyquaternium-6); |
| Diallyldimethyl ammonium salt copolymerized with acrylamide | (Polyquaternium-7); |
| Guarhydroxypropyltrimonium chloride | (Guarhydroxypropyltrimonium chloride); |
| Copolymer of N-vinylpyrrolidone and N,N-dimethylaminoethylmethacrylate, quaternized with dimethylsulfate | (Polyquaternium-11); |
| Copolymer of acrylamide and N,N-dimethylaminoethyl methacrylate, quaternized with dimethyl sulfate | (Polyquaternium-5); |
| Cationic hydroxyethylcellulosics | (Polyquaternium-10); |
| Cationic hydroxyethylcellulosics | (Polyquaternium-24); |
| Cetyltrimethylammonium chloride | (Cetrimonium chloride); |
| Decyldimethyloctylammonium chloride | (Quaternium-24); |
| Myristyltrimethylammonium chloride | (Mytrimonium chloride); |
| Polyoxyethylene(2)-cocomonium chloride | (PEG-2 Cocomonium chloride); |
| Methylbis(2-hydroxyethyl)cocoammonium chloride | (PEG-2 Cocoyl Quaternium-4); |
| Methylpolyoxyethylene-(15)cocoammonium chloride | (PEG-15 Cocoyl Quaternium-4); |
| Methylbis(2-hydroxyethyl)octadecyl ammonium chloride | (PEG-2 Stearyl Quaternium-4); |
| Methylpolyoxyethylene-(15)octadecylammonium chloride | (PEG-15 Stearyl Quaternium-4); |
| Methylbis(2-hydroxyethyl)-oleylammonium chloride | (PEG-2 Oleyl Quaternium-4); |
| Methylpolyoxyethylene-(15)oleylammonium chloride | (PEG-15 Oleyl quaternium-4); | wherein the name in parenthesis is the compound name given by the Cosmetic, Toiletry and Fragrance Association, Inc. in the *CTFA Cosmetic Ingredient Dictionary*, 3rd ed., 1982, hereinafter referred to as the *CTFA Dictionary*.

Similarly, the following list of oil-soluble quaternary ammonium compounds is exemplary, but not limiting, of oil-soluble, water-dispersible quaternary ammonium compounds that can be used in the method and composition of the present invention, either alone, in combination, or in combination with the water-soluble quaternary ammonium compounds:

| | |
|---|---|
| Cetyldimethylethylammonium bromide | (Cetethyldimonium bromide); |
| Cetyltrimethylammonium p-toluenesulfonate | (Cetrimonium tosylate); |
| Stearyldimethylbenzylammonium chloride | (Stearalkonium chloride); |
| Distearyldimethylammonium chloride | (Distearyldimonium chloride); |
| Dimethyldi(hydrogenated tallow)ammonium chloride | (Quaternium-18); |
| Cetyltrimethylammonium bromide | (Cetrimonium bromide); |
| Cetylethylmorpholinium ethosulfate | (Cetethylmorpholinium ethosulfate); |
| Behenyldimethylbenzylammonium chloride | (Behenalkonium chloride); |
| Behenyltrimethylammonium chloride | (Behentrimonium chloride); |
| Myristyltrimethylammonium bromide | (Mytrimonium bromide); | wherein the name in parenthesis is the compound name given in the *CTFA Dictionary*.

It should be noted that a long alkyl chain of the quaternary ammonium compound does not have to be solely, or primarily, of one chain length, i.e., the long chain need not be only lauryl ($C_{12}$), myristyl ($C_{14}$), stearyl ($C_{18}$) or behenyl ($C_{22}$). Rather, a quaternary ammonium compound wherein the long alkyl chain is a mixture of lengths can be used. Such quaternary ammonium conditioning agents are prepared conveniently from naturally-occurring materials, such as tallow, coconut oil, soya oil and the like, or from synthetically produced mixtures. Examples of water-soluble quaternary ammonium compounds having mixed carbon chain lengths include N-(soyaalkyl)-N,N,N-trimethyl ammonium chloride (soyatrimonium chloride); polyoxyethylene(2)cocomonium chloride (PEG-2 cocomonium chloride); and dimethyldi(hydrogenated tallow) ammonium chloride (Quaternium 18).

The quaternary ammonium compound is included in the clear hair-conditioner composition of the present invention in an amount of from about 0.5% to about 5% by weight of the composition. Preferably, the quaternary ammonium compound is present in an amount ranging from about 1% to about 4% by weight of the composition, and to achieve the full advantage of the present invention, the quaternary ammonium compound is present in an amount ranging from about 1% to about 2.5% by weight of the composition. It has been found that an amount of quaternary ammonium compound of at least about 0.5% by weight is necessary to provide a clear hair conditioning composition of the present invention that imparts an unexpectedly high degree of hair conditioning to treated hair.

The composition of the present invention also includes from about 0.5% to about 5%, and preferably from about 1% to about 4%, by weight of a volatile conditioning agent. In general, the volatile conditioning agent is added to the clear composition of the present invention in an amount sufficient to provide improved combing and improved feel of the treated hair. The volatile conditioning can be either a volatile, low molecular weight silicone or a volatile, low molecular weight hydrocarbon. The volatile low molecular weight silicone normally is a low molecular weight polydimethylsiloxane compound, however a low molecular weight polydimethylsiloxane including some phenyl substituents also is useful in the compositions of the present invention. Furthermore, the low molecular weight polydimethylsiloxane compound can be a linear or a cyclic polydimethylsiloxane compound, and can include phenyl substituents, as long as the polydimethylsiloxane compound provides sufficient lubrication and imparts hair conditioning properties to wet hair, and has sufficient volatility to slowly volatilize from the hair such that a residual buildup of silicone compound is not present on dry hair.

An example of a linear, low molecular weight, volatile polydimethylsiloxane compound useful in the composition and method of the present invention is the compound named in the *CTFA Dictionary* as hexamethyldisiloxane, available commercially under the tradename DOW CORNING 200 FLUID, from Dow Corning Corp., Midland, Michigan. Hexamethyldisiloxane has a viscosity of 0.65 cs (centistokes), is highly volatile, is nongreasy, provides lubrication, and improves the overall combing properties of the hair. Other linear polydimethylsiloxanes, such as decamethyltetrasiloxane, having a boiling point of about 195° C. and a viscosity of 1.5 centistokes; octamethyltrisiloxane; and dodecamethylpentasiloxane, also have sufficient volatility to be useful in the composition of the present invention, and are preferred over hexamethyldisiloxane due to a lower volatility than hexamethyldisiloxane. In general, it has been found that linear, low molecular weight, volatile polydimethylsiloxane compounds having a viscosity at 25° C. in the range of from about 0.5 cs to about 5 cs, and a boiling point at atmospheric pressure ranging from about 100° C. to about 250° C., are suitable for use in the clear hair-treating composition of the present invention.

In addition, the cyclic, low molecular weight, volatile polydimethylsiloxanes, named in the *CTFA Dictionary* as cyclomethicones, are useful in the clear composition and method of the present invention. The cyclomethicones useful in the present invention are low molecular weight, water-insoluble cyclic compounds having an average of about 3 to about 6 -[O-Si(CH$_3$)$_2$]- repeating group units per molecule and boil at atmospheric pressure in a range of from about 150° C. to about 250° C. The polydimethyl cyclosiloxanes having an average of about 4 to about 5 repeating units per molecule, i.e., the tetramer and pentamer, are preferred. To achieve the full advantage of the present invention, polydimethyl cyclosiloxanes having boiling points at atmospheric pressure in the range of 170° C. to 220° C., and viscosities at 25° C. of from about 2 to about 6 centistokes are included in the composition. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, New York, and SILICONE 334 FLUID and SILICONE 345 FLUID from Dow Corning Corporation, Midland, Michigan, the tetramer being listed first in each instance.

The volatile conditioning agent included in the composition of the present invention also can be a volatile hydrocarbon, such as a hydrocarbon including from about 10 carbon atoms to about 26 carbon atoms, that have sufficient volatility to slowly volatilize from the hair such that a residual buildup of hydrocarbon is not present on dry hair. The volatile hydrocarbon provides essentially the same benefits as the volatile silicone, such as lubrication and wet hair conditioning.

The preferred volatile hydrocarbon compound is an aliphatic hydrocarbon including from about 12 to about 24 carbon atoms, and has a boiling point in the range of from about 100° C. to about 300° C. Exemplary volatile hydrocarbons are depicted in general structural formula (V), wherein n ranges from 2 to 5,

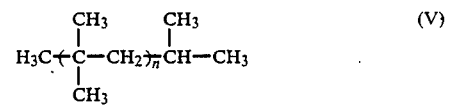

Examples of volatile hydrocarbons useful in the clear hair-conditioning composition of the present invention are the commercially-available compounds PERMETHYL 99A and PERMETHYL 101A, corresponding to compounds of general structure (V) wherein n is 2 and 3, respectively, from Permethyl Corporation, Frazer, PA. A volatile hydrocarbon compound is useful in the clear hair-conditioning composition of the present invention either alone, in combination with another volatile hydrocarbon, or in combination with a volatile silicone.

The above-described linear and cyclic volatile silicones, and volatile hydrocarbon compounds, have been used in hair-treating compositions and in various other cosmetic compositions, such as antiperspirants, deodorants, hair sprays, hair coloring products, hair grooming products, powder and color products and stick products because their low viscosity and low surface tension provide a light, silky feel on hair and skin. However, it is both new and unexpected for a volatile polydimethylsiloxane, or a volatile hydrocarbon compound, as described above, to be combined with a quaternary ammonium compound, an amidoamine compound of general structural formula (I) or (II), a solubilizing nonionic surfactant and a polyhydric compound to provide a clear, hair-conditioning composition that imparts such improved wet stage properties, dry stage properties, rinsing properties, and overall conditioning benefits to treated hair, like a reduction of split ends, improved body and improved manageability. Previous to the method and composition of the present invention, aqueous hair conditioners including a volatile silicone or a volatile hydrocarbon compound were emulsion-type products because of the inherent water-insolubility of the silicone and hydrocarbon compounds. Surprisingly and unexpectedly, the composition of the present invention is a stable and clear solution, or dispersion, of the volatile silicone and/or volatile hydrocarbon compound in an aqueous vehicle.

In addition to the quaternary ammonium compound and the volatile conditioning agent, the composition of the present invention also includes from about 0.1% to about 5%, and preferably from about 0.1% to about 2%, by weight of an amidoamine compound. In accordance with an important feature of the present invention, an amidoamine compound having the general structural formula (I) or (II):

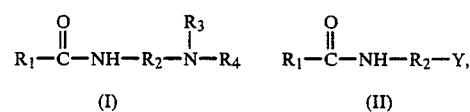

wherein R$_1$ is a fatty acid chain containing from about 11 to about 21 carbon atoms, R$_2$ is an alkylene group containing from two to about four carbon atoms, R$_3$ is hydrogen, methyl, ethyl or a hydroxyalkylene group containing from one to about three carbon atoms, R$_4$ is methyl, ethyl or a hydroxyalkylene group containing from one to about three carbon atoms, and Y is a heterocyclic nitrogen-containing moiety, like morpholine, is inclined, an solubilized, in a clear composition of the present invention to impart improved physical and cosmetic properties to hair.

An example of an amidoamine compound having the general structural formula (I) that is useful in the composition and method of the present invention is the compound named in the *CTFA Dictionary* as stearamidopropyldimethylamine, available commercially under the tradename LEXAMINE S-13 from Inolex Chemical Div., Philadelphia, PA, and having the structural formula (VI):

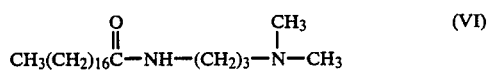

Other suitable amidoamine compounds include, but are not limited to, compounds designated in the *CTFA Dictionary* as stearamidoethyldiethanolamine, isostearamidopropylmorpholine, stearamidopropylmorpholine and stearamidoethylethanolamine, having structural formulas (VII), (VIII), (IX) and (X), respectively. In addition, suitable

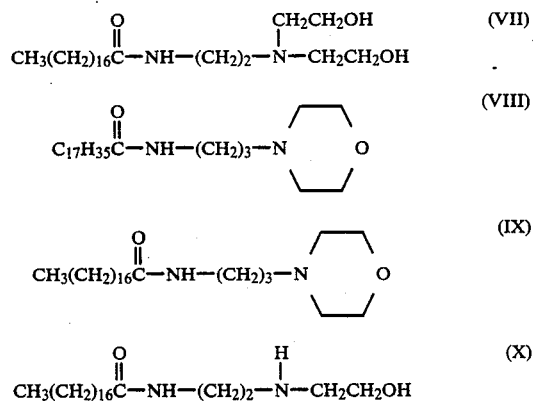

amidoamine compounds include compounds having either one or two hydroxymethyl, hydroxypropyl, methyl or ethyl moieties, or combinations thereof, present on an amino nitrogen in place of the hydroxyethyl moieties. Examples of such amidoamine compounds include, but are not limited to, dimethylaminopropyl stearamide, diethylaminoethyl stearamide, and dimethylaminopropyl myristamide.

The fatty acid chain $R_1$ of compounds of general structural formulas (I) and (II) does not have to be solely, or primarily, of one chain length, i.e., the long chain need not be derived only from lauryl ($C_{12}$), myristyl ($C_{14}$), cetyl ($C_{16}$), or stearyl ($C_{18}$). Rather, amidoamine compounds of general structural formulas (I) and (II) wherein the long alkyl chain is a mixture of lengths can be used. Such amidoamine compounds are prepared conveniently from naturally-occuring materials, such as tallow, coconut oil, soya oil and the like, or from synthetically produced mixtures.

In accordance with an important feature of the present invention, after adjustment of the composition pH with a suitable acid, the above-described amidoamine compounds of general structural formulas (I) and (II) exhibit the properties of a cationic surfactant. In the free amine state, as depicted in structural formulas (VI) through (X), the amidoamine compounds generally are insoluble in water. However, after pH adjustment, the amidoamine compounds exhibit increased water solubility. Consequently, in the neutralized state, the amidoamine compound behaves like a cationic surfactant, and therefore is substantive to the hair and imparts conditioning properties to the hair.

The acid used to adjust the pH of the composition can be essentially any organic acid or mineral acid. Such acids include, but are not limited to, hydrochloric acid, sulfuric acid, nitric acid, phosphoric acid, lactic acid, citric acid, tartaric acid, acetic acid, gluconic acid, glycolic acid and propionic acid, or combinations thereof. To achieve the full advantage of the present invention, the composition pH is adjusted with an organic acid, like lactic acid. In general, a sufficient amount of acid is added to adjust the final pH of the hair-treating composition to within a range of from about 4 to about 7, and more preferably to within a pH range of from about 5.5 to about 6.5.

In addition to the quaternary ammonium compound, the volatile conditioning agent and the amidoamine, the clear hair-conditioning composition of the present invention also includes a solubilizing nonionic surfactant. The solubilizing nonionic surfactant is present in the composition in an amount ranging from about 1% to about 10% by weight of the composition. The solubilizing nonionic surfactant is included in the composition to sufficiently solubilize the volatile conditioning compound, and to assist in solubilizing the amidoamine compound, such that the resulting conditioning composition is clear and homogeneous. In accordance with an important feature of the present invention, the solubilizing nonionic surfactant and volatile conditioning agent are present in the composition in a weight ratio of from at least about 1 to 1 and up to about 10 to 1. If the weight ratio of solubilizing nonionic surfactant to volatile conditioning agent is less than about 1 to 1, the volatile conditioning agent is not sufficiently solubilized to provide a clear hair-conditioning composition. Furthermore, if the weight ratio is greater than about 10 to 1, no further solubilizing benefits are realized and the solubilizing nonionic surfactant is present in excess and merely rinsed away from the hair without achieving any further solubilizing benefits or imparting any conditioning benefits. To achieve the full advantage of the present invention, a weight ratio of solubilizing nonionic surfactant to volatile condition agent in the range of from about 2 to 1 to about 4 to 1 provides a clear composition that imparts superior conditioning properties to the hair, without using an appreciable excess amount of solubilizing nonionic surfactant that eventually is wasted.

Suitable solubilizing nonionic surfactants include any nonionic surfactant that effectively solubilizes a volatile silicone conditioning compound or a volatile hydrocarbon conditioning compound that yields a clear, aqueous-based conditioner composition and that does not adversely affect either the quaternary ammonium compound, the amidoamine compound, or the volatile conditioning agent in regards to conditioning treated hair. Particular solubilizing nonionic surfactants found to be useful in the method and composition of the present invention include the N-alkylated-2-pyrrolidones of general structural formula XI, wherein $R_{12}$ is an alkyl moiety, straight chain or branched chain, including from about 8 to about 16 carbon atoms:

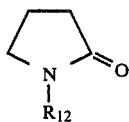
(XI)

Specific N-alkylated-2-pyrrolidones found useful in the composition of the present invention include decyl pyrrolidone (N-decyl-2-pyrrolidone) and lauryl pyrrolidone (N-dodecyl-2-pyrrolidone), available commercially under the tradenames SURFADONE LP-100 and SUFRADONE LP-300, respectively, from GAF Corporation, Wayne, NJ. Both SURFADONE LP-100 and SURFADONE LP-300 sufficiently solubilized the volatile conditioning agent to provide a clear conditioning composition that effectively imparted hair conditioning properties to treated hair.

The clear hair conditioning composition of the present invention also includes from about 10% to about 30% by weight of a polyhydric compound. Preferably, the clear hair-conditioning composition includes from about 15% to about 25% by weight of the polyhydric compound, and, to achieve the full advantage of the present invention, the composition includes from about 18% to about 22% by weight of the polyhydric compound. The polyhydric compound serves to couple the quaternary ammonium compound, the amidoamine compound, the volatile conditioning agent and the solubilizing nonionic surfactant to provide a clear, non-turbid, aqueousbased hair-conditioning composition. The polyhydric compound can be a glycol, a triol or a polyol. Specific examples include, but are not limited to, ethylene glycol, propylene glycol, butylene glycol, hexylene glycol, diethylene glycol, triethylene glycol, dipropylene glycol, tripropylene glycol, glycerol, or a polyethylene or polypropylene glycol having an average molecular weight up to approximately 500. It has been found that if the polyhydric compound is present in an amount of greater than about 30% by weight of the composition that the clarity of the composition is reduced. Furthermore, if the polyhydric compound is present in the composition in an amount below about 10% by weight, then the conditioner composition is not clear, unless an alcohol or other suitable organic cosolvent is included in the composition.

In addition to the five above-described essential ingredients, other common cosmetic components and additives that can be incorporated with the essential ingredients of the present invention, as long as the basic properties of the hair-treating composition, such as clarity of the composition and an ability to impart hair conditioning properties to hair, are not adversely affected. Such optional ingredients include, but not limited to, fragrances, dyes, hair colorants, dandruff control agents, hydrotropes, foam stabilizers, preservatives, water softening agents, acids, bases, buffers and the like. These optional components and additives usually will be present in weight percentages of less than about 2% each, and from about 5% to about 10% by weight of the composition in total.

The vehicle of the hair-treating composition is predominantly water, but organic solvents also can be included in order to facilitate manufacturing of the composition or to provide esthetic properties to the composition, such as viscosity control. Suitable solvents include the lower alcohols like ethyl alcohol and isopropyl alcohol; glycol ethers, like 2-butoxyethanol, ethylene glycol monoethyl ether, propylene glycol and diethylene glycol monoethyl ether or monomethyl ether; and mixtures thereof. These non-aqueous solvents can be present in the clear hair-conditioning composition of the present invention in an amount from about 1 to about 50% by weight and in particular from about 5 to about 25% by weight, relative to the total weight of the carrier vehicle in the composition.

The clear hair-conditioning compositions of the present invention also can be thickened, for example, with sodium alginate; guar gum; xanthan gum; gum arabic; cellulose derivatives such as methylcellulose, hydroxyethylcellulose, hydroxypropylmethylcellulose and carboxymethylcellulose; and various polymeric thickeners, such as polyacrylic acid derivatives. These thickeners are present in an amount ranging from about 0.1% to about 3%, and preferably from about 0.25% to about 1%, by weight relative to the total weight of the composition.

The clear hair-conditioning compositions also can include inorganic salts, humectants and similar materials to provide esthetic properties and desirable physical properties to the composition. Generally, such optional ingredients are present in weight percentages ranging from about 0.1% to about 10% each, and from about 0.1% to about 20% in total, relative to the total weight of the composition.

The compositions of the present invention are clear, relatively viscous compositions that are stable to phase separation at a temperature of about 25° C. for an indefinite period of time. For example, the clear compositions of the present invention have demonstrated sufficient stability to phase separation at temperatures normally found in commercial product storage and shipping to remain unaffected for periods of one year or more. Furthermore, upon a judicious selection of a liquid vehicle, it also is envisioned that a composition of the present invention can resist phase separation for even substantially longer storage periods. It also has been found that a clear, viscous composition has enhanced customer appeal compared to the present-day, emulsion-type conditioner compositions.

In accordance with the method of the present invention, several hair-treating compositions were prepared, then applied to human hair, to demonstrate the improved hair conditioning properties imparted by the clear compositions of the present invention comprising a quaternary ammonium compound; a volatile conditioning agent; an amidoamine compound of general structural formula (I) or (II); a solubilizing nonionic surfactant; and a polyhydric compound. It has been demonstrated that, to provide a clear composition and to maximize hair conditioning properties, the hair-treating composition of the present invention must include both a volatile conditioning agent, such as a volatile silicone, and a solubilizing nonionic surfactant. The volatile conditioning agent is pre-solubilized in the solubilizing nonionic surfactant, then this mixture is combined with the other composition ingredients to provide a clear conditioning composition. Surprisingly, the resulting clear hair-conditioning composition is more easily rinsed from the hair, and imparts excellent conditioning properties to the hair utilizing a lower amount of the conditioning agents. Consequently, the amount of conditioners coating the hair is decreased and residual conditioner buildup on the hair is reduced. Furthermore, as will be demonstrated hereinafter, laboratory and salon testing has shown that optimum conditioning properties are imparted to the hair when quaternary ammonium compound, an amidoamine compound and a solubilized volatile conditioning agent are present in the clear, conditioning composition in sufficient quantity.

For example, it has been found that at least about 0.5%, and preferably at least 1%, by weight of a quaternary ammonium compound should be present in the clear hair-conditioning compositions of the present invention. As will be discussed more fully hereinafter, it also has been found that an amount of quaternary ammonium compound in the composition above about 0.5% by weight further improves performance of the hair-conditioning composition up to a level of about 5% by weight of the quaternary ammonium compound. It further has been found that a level of quaternary ammonium compound in the composition above about 5% by weight, such as up to about 15% by weight, does not adversely affect composition performance, but may affect the clarity of the composition and also does not appreciably improve the performance of the hair-conditioning composition. Therefore, any amounts of quaternary ammonium compound in the composition above about 5% by weight are apparently wasted because the excess quaternary ammonium compound is rinsed from the hair during the rinsing step of the hair treatment.

To demonstrate the new and unexpected results achieved by treating hair with a clear conditioning composition comprising a quaternary ammonium compound; an amidoamine of general structural formula (I) or (II); a volatile, conditioning silicone or hydrocarbon; a solubilizing nonionic surfactant; and a polyhydric compound, the following compositions (Examples 1 through 12 in TABLE I) first were prepared. The method of manufacture of Examples 1 through 12 is essentially identical to the method of manufacturing the remaining Examples 13 through 30 and is described more fully hereinafter. Particular compositions of Examples 1 through 12 then were tested for their ability to condition hair. The particular quaternary ammonium compound used in Examples 1 through 12 was dicetyldimonium chloride, available under the tradename ADOGEN 432ET, from Sherex Chemical Co., Dublin, O. and including 70% by weight of dicetyldimonium chloride; the amidoamine compound used was stearamidopropyldimethylamine, available under the tradename LEXAMINE S-13, from Inolex Corp., Philadelphia, PA. and including 100% by weight of stearamidopropyldimethylamine; the volatile, low molecular weight polydimethylsiloxane compound used was cyclomethicone, available under the tradename SILICONE SF1173 from G. E. Silicones, Waterford, NY on a 100% by weight active ingredient basis. It should be understood that the following Examples 1 through 30 may not include particular essential ingredients of the clear hair-treating compositions of the present invention. Examples 1 through 24 were prepared and tested to help determine the limits of essential ingredients that can be present in the clear hair-treating compositions of the present invention, and the effects of omitting an essential ingredient from the hair-treating composition.

TABLE I

| INGREDIENT (% by weight) | EX.1 | EX.2 | EX.3 | EX.4 | EX.5 | EX.6 | EX.7 | EX.8 | EX.9 | EX.10 | EX.11 | EX.12 |
|---|---|---|---|---|---|---|---|---|---|---|---|---|
| Soft Water | 5.00 | 5.00 | — | — | 5.00 | — | — | — | — | — | — | — |
| ADOGEN 432ET (70% by wt. active) | 2.00 | 2.00 | — | 2.00 | 2.00 | 2.00 | 2.00 | 2.00 | 2.00 | 2.00 | 2.00 | 2.00 |
| SILICONE SF1173 (100% by wt. active) | 1.00 | 1.00 | 1.00 | 1.00 | 1.00 | 1.00 | 2.00 | 2.00 | 2.00 | 2.00 | 2.00 | 2.00 |
| SURFADONE LP300 (100% by wt. active) | 2.00 | 2.00 | 2.00 | 2.00 | 2.00 | 2.00 | 6.00 | 6.00 | 6.00 | 6.00 | 6.00 | 6.00 |
| LEXAMINE S-13 (100% by wt. active) | — | 0.80 | 0.80 | 0.80 | 0.80 | 0.80 | 0.80 | 0.80 | 0.80 | 0.80 | 0.80 | 0.80 |
| Lactic Acid (85% by wt. active) | — | 0.30 | 0.30 | 0.30 | 0.30 | 0.30 | 0.30 | 0.30 | 0.30 | 0.30 | 0.30 | 0.30 |
| Hexylene Glycol | — | — | 10.00 | 10.00 | — | 5.00 | 5.00 | 10.00 | 15.00 | 30.00 | 22.00 | 18.00 |
| Octoxynol-9[1] | 1.20 | 1.20 | 1.20 | 1.20 | 1.20 | 1.20 | 1.20 | 1.20 | 1.20 | 1.20 | 1.20 | 1.20 |
| Fragrance | 0.40 | 0.40 | 0.50 | 0.40 | 0.40 | 0.40 | 0.40 | 0.40 | 0.40 | 0.40 | 0.40 | 0.40 |
| Soft Water | 87.50 | 86.40 | 83.30 | 81.40 | 77.40 | 77.40 | 72.40 | 67.40 | 62.40 | 47.40 | 55.40 | 59.40 |
| Thickener[2] | 0.75 | 0.75 | 0.75 | 0.75 | 0.75 | 0.75 | 0.75 | 0.75 | 0.75 | 0.75 | 0.75 | 0.75 |
| Preservative[3] | 0.15 | 0.15 | 0.15 | 0.15 | 0.15 | 0.15 | 0.15 | 0.15 | 0.15 | 0.15 | 0.15 | 0.15 |
| Ethanol | | | | | 9.00 | 9.00 | 9.00 | 9.00 | 9.00 | 9.00 | 9.00 | 9.00 |
| Composition Appearance: | Emulsion | Emulsion | Slgty Turbid | Hazy | Hazy | Clear | Cldy | Slgty Turbid | Slgty Turbd | Clear | Clear | Clear |

| INGREDIENT (% by weight) | EX.13 | EX.14 | EX.15 | EX.16 | EX.17 | EX.18 | EX.19 | EX.20 | EX.21 | EX.22 | EX.23 | EX.24 |
|---|---|---|---|---|---|---|---|---|---|---|---|---|
| Soft Water | — | — | — | — | — | — | — | — | — | — | — | — |
| ADOGEN 432ET (70% by wt. active) | — | — | — | — | — | — | — | — | — | — | — | — |
| SILICONE SF1173 (100% by wt. active) | 1.00[4] | 1.00[4] | 1.00[4] | 1.00[4] | 1.00[4] | 1.00[4] | 1.00[4] | 1.00[4] | 1.00[4] | 1.00[5] | 1.00[5] | 1.00[6] |
| SURFADONE LP300 (100% by wt. active) | 5.00 | 5.00 | 4.00 | 3.00 | 3.00 | 4.00 | 10.00 | 4.00 | 10.00 | 5.00 | 4.00 | 5.00 |
| LEXAMINE S-13 (100% by wt. active) | 1.08 | 1.30 | 1.44 | 1.44 | 2.16 | — | — | — | — | 1.44 | 1.44 | 1.44 |
| Lactic Acid (85% by wt. active) | 0.41 | 0.49 | 0.54 | 0.54 | 0.81 | — | — | — | — | 0.54 | 0.54 | 0.54 |
| Hexylene | | | | | | | | | | | | |

TABLE I-continued

| | | | | | | | | | | | | |
|---|---|---|---|---|---|---|---|---|---|---|---|---|
| Glycol | 13.52 | 16.22 | 18.02 | 18.02 | 27.03 | 20.00 | 20.00 | — | — | 18.02 | 18.02 | 18.02 |
| Octoxynol-9[1] | — | — | — | — | — | — | — | — | — | — | — | — |
| Fragrance | — | — | — | — | — | — | — | — | — | — | — | — |
| Soft Water | 78.99 | 75.99 | 74.82 | 75.82 | 66.00 | 75.00 | 69.00 | 75.00 | 69.00 | 74.00 | 75.00 | 74.00 |
| Thickener[2] | — | — | — | — | — | — | — | — | — | — | — | — |
| Preservative[3] | — | — | — | — | — | — | — | — | — | — | — | — |
| Ethanol | — | — | — | — | — | — | — | 20.00 | 20.00 | — | — | — |
| Composition Appearance: | Clear | Clear | Clear | Slgty Turbid | Cldy Separates | Cldy Separates | Cldy Separates | Phase Separation | Cldy Separates | Clear | Clear | Cldy |

[1]TRITON X-100, Rohm and Haas Co., Philadelphia, PA.
[2]NATROSOL 250HNR, Hercules, Inc., Wilmington, DE. (hydroxyethylcellulose)
[3]0.05% KATHON CG, Rohm and Haas Co., Philadelphia, PA. and 0.10% GLYDANT, Lonza, Inc., Fairlawn, NJ.

Generally, the compositions of Examples 1 through 30 were prepared in an identical manner. For example, the composition of Example 1 was prepared by first producing a premix of the ADOGEN 432ET and a minor amount of soft water. Similarly, a second premix including the cyclomethicone and the SURFADONE LP300 was prepared. The two premixes then were combined and thoroughly admixed to form the main batch. Then a third premix of the octoxynol-9 and the fragrance was added to the main batch, and the resulting mixture was stirred until homogeneous. The thickener then was homogeneously dispersed in the major amount of soft water, and the aqueous thickener dispersion was added to the main batch. After thorough blending, the preservative was added to the resulting composition. The composition of Example 1, lacking the amidoamine compound and the polyhydric compound was an emulsion-type product.

Similarly, the composition of Example 6 was prepared by first producing a premix including the hexylene glycol, the LEXAMINE S-13 and the lactic acid. The premix was heated to about 150° F. to about 165° F., then held at the elevated temperature for about 30 minutes. After cooling to about 100° F., a second premix including the ADOGEN 432ET and ethanol was added to the first premix, and the two premixes were thoroughly blended until homogeneous. Then a previously prepared dispersion of the thickener and the major portion of the soft water was added to the homogeneous premix blend to form the main batch. Next, a previously-prepared third premix of the cyclomethicone and SURFADONE LP300 was added to the main batch, followed by the addition of a fourth premix including the octoxynol-9 and fragrance. After thorough blending to produce a clear, homogeneous composition, the preservative was added to produce the composition of Example 6.

It was found that Examples 1 and 2, each absent the polyhydric compound, i.e., hexylene glycol, were emulsions as opposed to clear compositions. Similarly, Example 3, including the hexylene glycol but absent the quaternary ammonium compound, ADOGEN 432ET, produced a hazy composition. Example 4, including each of the five essential ingredients of the present invention, was a hazy composition, thereby showing that at least about 10% of the polyhydric compound should be present in the composition. However, Example 6 demonstrates that the amount of polyhydric compound can be reduced to below 10%, if an alcohol also is included in the composition. Example 5 demonstrates that an alcohol alone does not produce a clear composition, therefore requiring that a polyhydric compound be present in the composition. Examples 7 through 12 demonstrate that increased amounts of hexylene glycol further clarify the composition, with a clear composition resulting over the range of from about 10% to about 30% by weight hexylene glycol, and with maximum clarity achieved at polyhydric compound levels of from about 18% to about 22% by weight of the composition.

Examples 13 through 24 were prepared to demonstrate the effect of omitting one of the essential ingredients from the composition, and to demonstrate the effect of varying the amount of the essential ingredients in the composition. Therefore, Example 13 shows that a composition including only water and four of the five essential ingredients, adjusted to the proper pH, provides a clear conditioning composition if the ratio of SURFADONE LP300 to cyclomethicone is sufficiently high. Examples 13 through 15 demonstrate that the amount of amidoamine compound, LEXAMINE S-13, and/or the amount of the solubilizing nonionic surfactant, SURFADONE LP300, can be varied to yield a clear conditioning composition when the SURFADONE/silicone ratio is at least about 4 to 1 even though the ADOGEN 432ET is absent. Examples 14 through 17 show that if the amount of amidoamine is increased significantly, and the ratio of SURFADONE LP300 to cyclomethicone is significantly reduced, a clear composition absent the quaternary ammonium compound does not result.

Examples 18 through 21 demonstrate the effect of eliminating at least one of the essential ingredients from the composition. In each of Examples 18 through 21, the composition was opaque and unstable, separating into distinct aqueous and nonaqueous phases within a short time period. Example 21 further shows that an alcohol alone will not solubilize the cyclomethicone and SURFADONE LP300, and Example 19 shows that the polyhydric compound alone will not solubilize the cyclomethicone and SURFADONE LP300. Examples 22 through 24 showed that linear volatile silicones, either dimethylpolysiloxanes or phenyl-substituted dimethylpolysiloxanes are useful as the volatile conditioning agent of the composition of the present invention.

In addition, Examples 25 through 29 in TABLE II show that a volatile hydrocarbon can be used as the volatile conditioning agent in a clear hair-conditioning composition of the present invention. The compositions of Examples 25 through 29 were produced by a method similar to producing the compositions of Examples 1 through 24.

TABLE II

| Ingredient (% by weight) | EX.25 | EX.26 | EX.27 | EX.28 | EX.29 |
| --- | --- | --- | --- | --- | --- |
| Soft Water | 76.00 | 75.00 | 75.99 | 78.99 | 74.00 |
| Volatile Hydrocarbon[1] | 1.00 | 1.00 | 1.00 | 1.00 | 1.00 |
| SURFADONE LP300 (100% by wt. active) | 3.00 | 4.00 | 5.00 | 5.00 | 5.00 |
| Hexylene Glycol | 18.02 | 18.02 | 16.22 | 13.52 | 18.02 |
| LEXAMINE S13 (100% by wt. active) | 1.44 | 1.44 | 1.30 | 1.08 | 1.44 |
| Lactic Acid (85% by wt. active) | 0.54 | 0.54 | 0.49 | 0.41 | 0.54 |
| Composition Appearance: | Clear | Clear | Cloudy | Cloudy | Clear |

[1]The volatile hydrocarbon used is an isoparaffinic hydrocarbon including about 12 carbon atoms, sold under the tradename PERMETHYL 99A, available from Permethyl Corp., Frazer, PA.

From Examples 25 through 29 in TABLE II, it was observed that a volatile hydrocarbon can be used as the volatile conditioning agent to provide a clear conditioning composition of the present invention (EXS. 25, 26 and 29). However, conditioning compositions including a volatile hydrocarbon as the volatile conditioning apparently are more sensitive to the amount of polyhydric compound present in the composition. Examples 27 and 28 show that, even if the ratio of SURFADONE LP300 to volatile hydrocarbon is relatively high, the composition is cloudy unless a sufficient amount of polyhydric compound is included in the composition.

To demonstrate that clear hair-conditioning compositions including a quaternary ammonium compound, an amidoamine of general structural formula (I) or (II), a volatile conditioning agent, a solubilizing nonionic surfactant and a polyhydric compound effectively impart hair conditioning properties to treated hair, particular compositions of Examples 1 through 12 were applied to hair. These particular compositions were compared to two leading commercial hair conditioners, HAIR SPECIFICS and FINESSE, both available from Helene Curtis, Inc., Chicago, IL., for an ability to impart hair conditioning properties the hair. In contrast to the clear conditioning compositions of the present invention (i.e., Example 12), both HAIR SPECIFICS and FINESSE are traditional emulsion-type hair conditioner products.

In particular, to demonstrate the improved hair conditioning properties imparted to hair treated with the composition of the present invention, the composition of Example 12 was applied to human hair and conditioning properties were compared to the condition properties imparted by FINESSE or HAIR SPECIFICS. A group of five trained judges rated hair treated with the composition of Example 12 and either the commercially-available hair conditioner FINESSE or the commercially-available hair conditioner HAIR SPECIFICS in a salon evaluation. FINESSE includes a quaternary ammonium compound, an amidoamine compound and a polydimethylsiloxane in a total amount of about 4.4% by weight. HAIR SPECIFICS includes a quaternary ammonium compound, dimethicone and a quaternized protein in a total amount of about 4% by weight. Both HAIR SPECIFICS and FINESSE are commercially available, with FINESSE being recognized as an exceptional hair conditioning product and HAIR SPECIFICS being recognized as a premium hair conditioning product. It should be noted that in this subjective salon testing, if a composition imparts hair conditioning properties to treated hair equivalent to the properties imparted by FINESSE, the composition is considered an exceptional conditioner because FINESSE is recognized as a benchmark for hair conditioning performance. Accordingly, if a composition imparts hair conditioning properties to treated hair equivalent to properties imparted by HAIR SPECIFICS, the composition is considered a premium conditioner because HAIR SPECIFICS is recognized as a superior hair-conditioner, but not as efficacious as FINESSE.

In general, in a salon test the composition of interest is applied to one side of a head of hair, and the product used for comparison, i.e., either FINESSE or HAIR SPECIFICS, is applied to the other side of the head. After the treatment, each side of hair is judged for a variety of hair conditioning properties by a panel of five trained judges on a ranking of 1 unit (worst) to 5 units (best). Then ratings of the judges for each hair conditioning property are averaged, and a difference in rating one side of hair compared to the other side of hair of at least 0.3 units is considered a significant difference for that particular hair conditioning property. The judges rate the hair for such hair conditioning properties as ease of application, fragrance, ease of rinsing, wet feel, wet comb, residue, dry combing, dry feel, coating, flakes/dust, static, manageability, condition of ends, sheen/luster, body, effect on hair color, irritation and overall condition.

Accordingly, a clear composition of the present invention, including 2% by weight ADOGEN 432ET, 1% by weight cyclomethicone, 2% by weight SURFADONE LP300, 0.8% by weight LEXAMINE S-13 and 10% by weight hexylene glycol (Ex. 30), was compared to the HAIR SPECIFICS conditioner. It was found that in a salon comparative test of the composition of Example 30 and HAIR SPECIFICS conditioner, that a significant improvement (i.e., at least 0.3 rating units) in wet feel, dry feel, dry combing, coating, manageability, condition of ends, and overall condition was found in hair treated with the composition of Example 30. It should be noted that among the numerous hair conditioning properties, these properties are considered key properties in regard to hair conditioning. Furthermore, for each of the twenty-one conditioning properties that were compared, the composition of Example 30 at least equalled the conditioning properties imparted by HAIR SPECIFICS.

In addition, an identical salon comparative test was performed between the composition of Example 30 and FINESSE. In this comparative test, the composition of Example 30 and FINESSE compared essentially identically, except that FINESSE demonstrated a 0.3 unit superiority in dry combing and dry feel. For all the remaining hair conditioning properties, the ratings between the composition of Example 30 and FINESSE were identical or less than the significant difference of 0.3 rating units. Considering the exceptional hair conditioning properties imparted to hair by FINESSE, it is both surprising and unexpected for a composition of the present invention (EX. 30) to impart essentially the identical hair conditioning properties to treated hair. Overall, the above salon comparative tests demonstrate that the clear conditioning compositions of the present invention, including a quaternary ammonium compound, a volatile conditioning agent, an amidoamine compound, a solubilizing nonionic surfactant, and a polyhydric compound, surprisingly and unexpectedly possess an improved ability to impart hair conditioning properties to hair.

Therefore, the method and composition of the present invention impart exceptional hair conditioning properties to treated hair usually demonstrated only by premium hair conditioner compositions. It is both surprising and unexpected for an aqueous composition of the present invention, including a water-insoluble volatile conditioning agent, to be a consumer-appealing clear product, to maintain product stability over long storage times, and to impart such excellent hair conditioning properties to treated hair. The clear compositions of the present invention coat the hair more effectively and also are especially easy to rinse from the hair. Consequently, an improved and more effective coating of the hair requires less conditioner composition to be applied to the hair, thereby also reducing the amount of dulling, chemical residue that coats the hair shaft.

In addition, the method of the present invention provides the further benefits of not leaving the hair tacky or sticky; not forming a crust and therefore providing combability; and providing manageable and styleable hair having body. In addition, after treating the hair with the composition of the present invention, the hair feels natural and thickened, has body, is soft, shiny, manageable, and combable. These beneficial effects can be achieved by using an aqueous spray or aqueous solution formulation.

Obviously, many modifications and variations of the invention as hereinbefore set forth can be made without departing from the spirit and scope thereof and therefore only such limitations should be imposed as are indicated by the appended claims.

I claim:

1. A hair-conditioning composition comprising:
   (a) from about 0.5% to about 5% by weight of a quaternary ammonium compound, wherein the quaternary ammonium compound has a general structure:

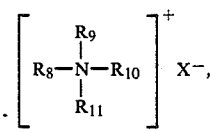

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;
   (b) from about 0.1% to about 5% by weight of an amidoamine compound, wherein the amidoamine compound has a general structure:

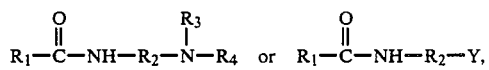

wherein $R_1$ is a fatty acid chain containing from about 11 to about 21 carbon atoms; $R_2$ is an alkylene group containing from two to about four carbon atoms; $R_3$ is hydrogen, a methyl group an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety;
   (c) from about 0.5% to about 5% by weight of a volatile conditioning agent selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 centistokes to about 6 centistokes and a boiling point at atmospheric pressure ranging from about 150° C. to about 250° C., an aliphatic hydrocarbon having from about 10 carbon atoms to 26 carbon atoms and a boiling point at atmospheric pressure in the range of from about 100° C. to about 300° C., and mixtures thereof;
   (d) from about 1% to about 10% by weight of a nonionic surfactant capable of solubilizing the volatile conditioning agent;
   (e) from about 10% to about 30% by weight of a polyhydric alcohol selected from the group consisting of glycols, triols, polyols and mixtures thereof; and
   (f) a suitable liquid vehicle; wherein the weight ratio of the nonionic surfactant to the volatile conditioning agent is at least 1 to 1 and the pH of the composition is in the range of from about 4 to about 7.

2. The hair-conditioning composition of claim 1 wherein the nonionic surfactant and the volatile conditioning agent are present in a weight ratio of nonionic surfactant to volatile conditioning agent ranging from at least 1 to 1 to about 10 to 1.

3. The hair-conditioning composition of claim 2 wherein the nonionic surfactant and the volatile conditioning agent are present in a weight ratio ranging from about 2 to 1 to about 5 to 1.

4. The hair-conditioning composition of claim 1 wherein the composition includes the quaternary ammonium compound in an amount ranging from about 1% to about 4% by weight of the composition.

5. The hair-conditioning composition of claim 1 wherein the composition includes the quaternary ammonium compound in an amount ranging from about 1% to about 2.5% by weight of the composition.

6. The hair-conditioning composition of claim 1 wherein the quaternary ammonium compound is selected from the group consisting of laurtrimonium chloride; Quaternium-16; lauralkonium chloride; olealkonium chloride; dilauryldimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; Polyquaternium-11; Polyquaternium-5; Polyquaternium-10;

Polyquaternium-24; cetrimonium chloride; Quaternium-24; mytrimonium chloride; PEG-2 Cocomonium chloride; PEG-2 Cocoyl Quaternium-4; PEG-15 Cocoyl Quaternium-4; PEG-2 Stearyl Quaternium-4; Peg-15 Stearyl Quaternium-4; Peg-2 Oleyl Quaternium-4; PEG-15 Oleyl Quaternium-4; cetethyldimonium bromide; cetrimonium tosylate; stearalkonium chloride; distearyldimonium chloride; Quaternium-18; cetrimonium bromide; cetethylmorpholinium ethosulfate; benhenalkonium chloride; behentrimonium chloride; mytrimonium bromide; and combinations thereof.

7. The hair-conditioning composition of claim 1 wherein the quaternary ammonium compound is selected from the group consisting of cetrimonium chloride; laurtrimonium chloride; Quaternium-16; laurylpyridinium chloride; mytrimonium chloride; Quaternium-24; soyatrimonium chloride; cetylpyridinium chloride; cetalkonium chloride; olealkonium chloride; dicetyldimonium chloride; lauralkonium chloride; Polyquaternium-11; distearyldimonium chloride; stearalkonium chloride; behenalkonium chloride; mytrimonium bromide, cetethylmorpholinium ethosulfate; and combinations thereof.

8. The hair-conditioning composition of claim 1 wherein the composition includes the amidoamine compound in an amount ranging from about 0.1% to about 2% by weight of the composition.

9. The hair-conditioning composition of claim 1 wherein the amidoamine compound is selected from the group consisting of stearamidoethylethanolamine, stearamidoethyldiethanolamine, isostearamidopropylmorpholine, stearamidopropylmorpholine, stearamidopropyldimethylamine, diethylaminoethyl stearamide, dimethylaminopropyl myristamine, and combinations thereof.

10. The hair-conditioning composition of claim 1 wherein the volatile conditioning agent is present in an amount ranging from about 1% to about 4% by weight of the composition.

11. The hair-conditioning composition of claim 1 wherein the linear polydimethylsiloxane is selected from the group consisting of hexamethyldisiloxane, octamethyltrisoloxane, decamethyltetrasiloxane and combinations thereof.

12. The hair-conditioning composition of claim 1 wherein the cyclic polydimethylsiloxane is selected from the group consisting of hexamethylcyclotrisiloxane, octamethylcyclotetrasiloxane, decamethylcyclopentasiloxane, dodecamethylcyclohexasiloxane and combinations thereof.

13. The hair-conditioning composition of claim 1 wherein the volatile hydrocarbon is a low molecular weight aliphatic hydrocarbon including from about 12 carbon atoms to about 16 carbon atoms.

14. The hair-conditioning composition of claim 1 wherein the volatile conditioning agent is an aliphatic hydrocarbon having the general structural formula

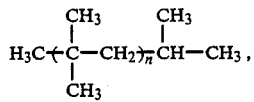

wherein n ranges from 2 to 5, and mixtures thereof.

15. The hair-conditioning composition of claim 1 wherein the nonionic surfactant is an N-alkylated pyrrolidone.

16. The hair-conditioning composition of claim 15 wherein N-alkylated pyrrolidone includes an alkyl group having from about 10 carbon atoms to about 16 carbon atoms.

17. The hair-conditioning composition of claim 15 wherein N-alkylated pyrrolidone is lauryl pyrrolidone, decyl pyrrolidone or a combination thereof.

18. The hair-conditioning composition of claim 1 wherein the polyhydric compound is present in an amount ranging from about 15% to about 25% by weight of the composition.

19. The hair-conditioning composition of claim 1 wherein the polyhydric compound is present in an amount ranging from about 18% to about 22% by weight of the composition.

20. The hair-conditioning composition of claim 1 wherein the polyhydric compound is selected from the group consisting of ethylene glycol, propylene glycol, butylene glycol, hexylene glycol, glycerol, diethylene glycol, triethylene glycol, dipropylene glycol, tripropylene glycol, polypropylene glycol having an average molecular weight of up to approximately 500, polyethylene glycol having an average molecular weight of up to approximately 500, and mixtures thereof.

21. The hair-conditioning composition of claim 1 wherein the suitable liquid vehicle comprises water.

22. The hair-conditioning composition of claim 21 wherein the liquid vehicle further comprises from about 1% to about 50% by weight relative to the total weight of the liquid vehicle of a lower alcohol, a glycol ether, or a combination thereof.

23. The hair-conditioning composition of claim 21 wherein the liquid vehicle further comprises from about 5% to about 25% by weight relative to the total weight of the liquid vehicle of a lower alcohol, a glycol ether, or a combination thereof.

24. The hair-conditioning composition of claim 22 wherein the liquid vehicle further comprises from about 1% to about 50% by weight relative to the total weight of the liquid vehicle of ethyl alcohol, isopropyl alcohol, 2-butoxyethanol, ethylene glycol monoethyl ether, diethylene glycol monoethyl ether, diethylene glycol monomethyl ether or combinations thereof.

25. The hair-conditioning composition of claim 1 wherein the composition has a pH of from about 5.5 to about 6.5.

26. The hair-conditioning composition of claim 1 wherein the quaternary ammonium compound is dicetyldimonium chloride; the amidoamine compound is stearamidopropyldimethylamine; the volatile conditioning agent is cyclomethicone; the nonionic surfactant is lauryl pyrrolidone; and the polyhydric compound is hexylene glycol.

27. A hair-conditioning composition comprising:
(a) 0.5% to about 5% by weight of dicetyldimonium chloride;
(b) from about 0.1% to about 5% by weight of stearamidopropyldimethylamine;
(c) from about 0.5% to about 5% by weight of cyclomethicone;
(d) from about 1% to about 10% of lauryl pyrrolidone;
(e) from about 15% to about 25% by weight of hexylene glycol; and
(f) a suitable liquid vehicle; wherein the weight ratio of lauryl pyrrolidone to cyclomethicone is in the range of from about 2 to 1 to about 5 to 1 and the composition has a pH in the range of from about 5.5 to about 6.5

28. A method of treating hair comprising contacting the hair for a sufficient time with a transparent hair-conditioning composition comprising:
(a) from about 0.5% to about 5% by weight of a quaternary ammonium compound, wherein the quaternary ammonium compound has a general structure:

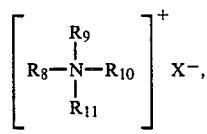

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;
(b) from about 0.1% to about 5% by weight of an amidoamine compound, wherein the amidoamine compound has a general structure;

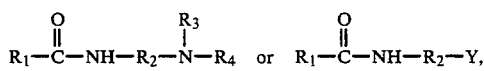

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety;
(c) from about 0.5% to about 5% by weight of a volatile conditioning agent selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 centistokes to about 6 centistokes and a boiling point at atmospheric pressure ranging from about 150° C. to about 250° C., an aliphatic hydrocarbon having from about 10 carbon atoms to 26 carbon atoms and a boiling point at atmospheric pressure in the range of from about 100° C. to about 300° C., and mixtures thereof;
(d) from about 1% to about 10% by weight of a nonionic surfactant capable of solubilizing the volatile conditioning agent;
(e) from about 10% to about 30% by weight of a polyhydric alcohol selected from the group consisting of glycols, triols, polyols and mixtures thereof; and
(f) a suitable liquid vehicle, wherein the weight ratio of the nonionic surfactant to the volatile conditioning agent is at least 1 to 1 and the pH of the composition is in the range of from about 4 to about 7, to impart hair-conditioning properties to the hair.

29. A method of imparting conditioning properties to hair comprising contacting the hair for a time sufficient for the hair to interact with a composition comprising:
(a) from about 0.5% to about 5% by weight of a quaternary ammonium compound, wherein the quaternary ammonium compound has a general structure:

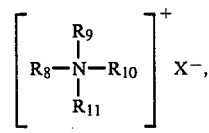

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group: $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;
(b) from about 0.1% to about 5% by weight of an amidoamine compound, wherein the amidoamine compound has a general structure:

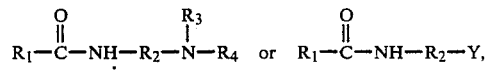

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group consisting from one to about three carbon atoms; and Y is an organic heterocyclic nitrogen-containing moiety;
(c) from about 0.5% to about 5% by weight of a volatile conditioning agent selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 centistokes to about 6 centistokes and a boiling point at atmospheric pressure ranging from about 150° C. to about 250° C., an aliphatic hydrocarbon having from about 10 carbon atoms to 26 carbon atoms and a boiling point at atmospheric pressure in the range of from about 100° C. to about 300° C., and mixtures thereof;

(d) from about 1% to about 10% by weight of a nonionic surfactant capable of solubilizing the volatile conditioning agent;

(e) from about 10% to about 30% by weight of a polyhydric alcohol selected from the group consisting of glycols, triols, polyols and mixtures thereof; and (f) a suitable liquid vehicle; wherein the weight of the nonionic surfactant to the volatile conditioning agent is at least 1 to 1 and the pH of the composition is in the range of from about 4 to about 7.

30. The method of claim 29 further comprising rinsing the hair with water after contacting the hair with the composition.

31. A hair-conditioning composition comprising:

(a) from about 0.5% to about 5% by weight of a quaternary ammonium compound, wherein the quaternary ammonium compound has a general structure:

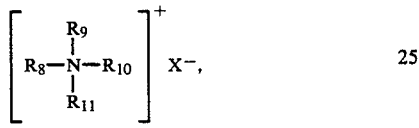

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;

(b) from about 0.1% to about 5% by weight of an amidoamine compound, wherein the amidoamine compound has a general structure;

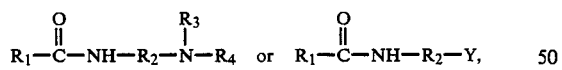

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety;

(c) from about 0.5% to about 5% by weight of a volatile conditioning agent selected from the group consisting of a linear polydimethylsiloxane having a viscosity at 25° C. in the range from about 0.5 centistokes to about 5 centistokes and a boiling point at atmospheric pressure ranging from about 100° C to about 250° C, a cyclic polydimethylsiloxane having a viscosity at 25° C. of from about 2 centistokes to about 6 centistokes and a boiling point at atmospheric pressure ranging from about 150° C. to about 250° C., an aliphatic hydrocarbon having from about 10 carbon atoms to 26 carbon atoms and a boiling point at atmospheric pressure in the range of from about 100° C. to about 300° C., and mixtures thereof;

(d) from about 1% to about 10% by weight of a nonionic surfactant capable of solubilizing the volatile conditioning agent, wherein the nonionic surfactant is an N-alkylated pyrrolidone;

(e) from about 10% to about 30% by weight of a polyhydric alcohol selected from the group consisting of glycols, triols, polyols and mixtures thereof; and (f) a suitable liquid vehicle; wherein the weight of the nonionic surfactant to the volatile conditioning agent is at least 1 to 1 and the pH of the composition is in the range of from about 4 to about 7.

32. A hair-conditioning composition comprising:

(a) from about 0.5% to about 5% by weight of a quaternary ammonium compound, wherein the quaternary ammonium compound has a general structure:

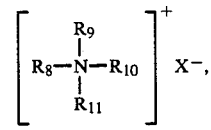

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;

(b) from about 0.1% to about 5% by weight of an amidoamine compound, wherein the amidoamine compound has a general structure:

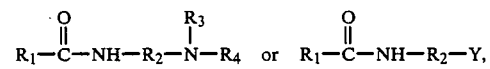

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety;

(c) from about 0.5% to about 5% by weight of a volatile conditioning agent selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 centistokes to about 6 centistokes and a boiling point at atmospheric pressure ranging from about 150° C. to about 250° C., an aliphatic hydrocarbon having from about 10 carbon atoms to 26 carbon atoms and a boiling point at atmospheric pressure in the range of from about 100° C. to about 300° C., and mixtures thereof;

(d) from about 1% to about 10% by weight of a nonionic surfactant capable of solubility the volatile conditioning agent selected from the group consisting of N-alkyl pyrrolidones having an alkyl group containing from about 10 carbon atoms to about 16 carbon atoms;

(e) from about 10% to about 30% by weight of a polyhydric alcohol selected from the group consisting of glycols, triols, polyols and mixtures thereof; and (f) a suitable liquid vehicle; wherein the weight of the nonionic surfactant to the volatile conditioning agent is at least 1 to 1 and the pH of the composition is in the range of from about 4 to about 7.

33. A method of treating hair comprising contacting the hair for a sufficient time with a transparent hair-conditioning composition comprising:

(a) from about 0.5% to about 5% by weight of a quaternary ammonium compound, wherein the quaternary ammonium compound has a general structure:

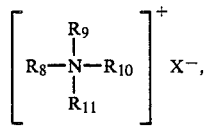

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;

(b) from about 0.1% to about 5% by weight of an amidoamine compound, wherein the amidoamine compound has a general structure:

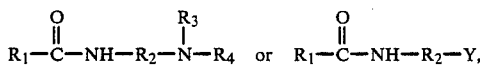

wherein $R_1$ is a fatty acid chain containing from about 11 to about 21 carbon atoms; $R_2$ is an alkylene group containing from two to about four carbon atoms; $R_3$ is a hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety;

(c) from about 0.5% to about 5% by weight of a volatile conditioning agent selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 centistokes to about 6 centistokes and a boiling point at atmospheric pressure ranging from about 150° C. to about 250° C., an aliphatic hydrocarbon having from about 10 carbon atoms to 26 carbon atoms and a boiling point at atmospheric pressure in the range of from about 100° C. to about 300° C., and mixtures thereof;

(d) from about 15 to about 10% by weight of a nonionic surfactant capable of solubilizing the volatile conditioning agent selected from the group consisting of N-alkyl pyrrolidones having an alkyl group containing from about 10 carbon atoms to about 16 carbon atoms;

(e) from about 10% to about 30% by weight of a polyhydric alcohol selected from the group consisting of glycols, triols, polyols and mixtures thereof; and (f) a suitable liquid vehicle; wherein the weight of the nonionic surfactant to the volatile conditioning agent is at least 1 to 1 and the pH of the composition is in the range of from about 4 to about 7, to impart hair-conditioning properties to the hair.

34. A hair-conditioning composition comprising:

(a) from about 0.5% to about 5% by weight of a quaternary ammonium compound, wherein the quaternary ammonium compound has a general structure:

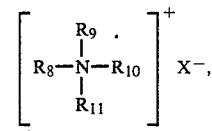

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;

(b) from about 0.1% to about 5% by weight of an amidoamine compound, wherein the amidoamine compound has a general structure:

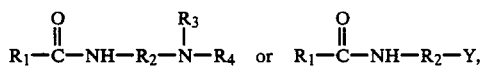

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety;

(c) from about 0.5% to about 5% by weight of a volatile conditioning agent selected from the group consisting of a volatile silicones, volatile hydrocarbons and mixtures thereof having a boiling point at atmospheric pressure ranging from about 100° C. to about 300° C;

(d) from about 1% to about 10% by weight of a nonionic surfactant capable of solubilizing the volatile conditioning agent;

(e) from about 10% to about 30% by weight of a polyhydric alcohol selected from the group consisting of glycols, triols, polyols and mixtures thereof; and (f) a suitable liquid vehicle; wherein the weight of the nonionic surfactant to the volatile conditioning agent is at least 1 to 1 and the pH of the composition is in the range of from about 4 to about 7.

35. A method of treating hair comprising contacting the hair for a sufficient time with a transparent hair-conditioning composition comprising:

(a) from about 0.5% to about 5% by weight of a quaternary ammonium compound, wherein the quaternary ammonium compound has a general structure:

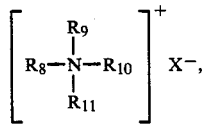

wherein $R_8$ is an alkyl group including from about 8 to about 22 carbon atoms; $R_9$ is selected from the group consisting of an alkyl group including from about 8 to about 22 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, bromide, methosulfate, ethosulfate, tosylate, acetate, phosphate and nitrate;

(b) from about 0.1% to about 5% by weight of an amidoamine compound, wherein the amidoamine compound has a general structure:

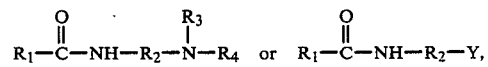

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety;

(c) from about 0.5% to about 5% by weight of a volatile conditioning agent selected from the group consisting of volatile silicones, volatile hydrocarbons and mixtures thereof having a boiling point at atmospheric pressure ranging from about 100° C. to about 300° C;

(d) from about 1% to about 10% by weight of a nonionic surfactant capable of solubilizing the volatile conditioning agent;

(e) from about 10% to about 30% by weight of a polyhydric alcohol selected from the group consisting of glycols, triols, polyols and mixtures thereof; and (f) a suitable liquid vehicle; wherein the weight of the nonionic surfactant to the volatile conditioning agent is at least 1 to 1 and the pH of the composition is in the range of from about 4 to about 7, to impart hair-conditioning properties to the hair.

* * * * *